United States Patent
Horvath et al.

(10) Patent No.: US 8,292,434 B2
(45) Date of Patent: Oct. 23, 2012

(54) WHITE LIGHT EMITTING DIODE (LED) ILLUMINATOR FOR OPHTHALMIC ENDOILLUMINATION

(75) Inventors: Christopher Horvath, Lake Forest, CA (US); Michael J. Papac, Tustin, CA (US); Ronald T. Smith, Irvine, CA (US); Michael J. Yadlowsky, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 240 days.

(21) Appl. No.: 12/845,216

(22) Filed: Jul. 28, 2010

(65) Prior Publication Data
US 2011/0037948 A1    Feb. 17, 2011

Related U.S. Application Data

(60) Provisional application No. 61/233,285, filed on Aug. 12, 2009.

(51) Int. Cl.
*A61B 3/10* (2006.01)
*A61B 3/00* (2006.01)

(52) U.S. Cl. ........... 351/221; 351/213; 351/246; 606/15

(58) Field of Classification Search .................. 351/221, 351/213, 246; 606/11, 15–16; 600/178; 359/385
See application file for complete search history.

(56) References Cited

U.S. PATENT DOCUMENTS

| | | |
|---|---|---|
| 6,183,086 B1 | 2/2001 | Neubert |
| 2002/0087149 A1 | 7/2002 | McCary |
| 2004/0090796 A1 | 5/2004 | Steen et al. |
| 2008/0030984 A1 | 2/2008 | Harbers et al. |
| 2008/0246920 A1 | 10/2008 | Buczek et al. |
| 2008/0262316 A1 * | 10/2008 | Ajima et al. .................. 600/178 |
| 2009/0182313 A1 | 7/2009 | Auld |
| 2009/0203966 A1 * | 8/2009 | Mizuyoshi .................... 600/182 |
| 2010/0182569 A1 * | 7/2010 | Artsyukhovich et al. ..... 351/221 |
| 2011/0037949 A1 * | 2/2011 | Papac et al. .................. 351/221 |
| 2011/0038174 A1 * | 2/2011 | Papac et al. .................. 362/572 |
| 2011/0122366 A1 * | 5/2011 | Smith ........................... 351/221 |

* cited by examiner

*Primary Examiner* — Jordan Schwartz
(74) *Attorney, Agent, or Firm* — Keiko Ichiye

(57) ABSTRACT

An ophthalmic endoilluminator is provided. The ophthalmic endoilluminator includes one or more white light emitting diodes (LEDs), an additional light source, a first optical assembly, an optical coupling element, and an optical fiber optically coupled to the optical coupling element. The white LED is capped with a phosphor layer. The additional light source illuminates at least a portion of an exterior surface of the phosphor layer within an absorption band of phosphor material of the phosphor layer in order to excite the phosphor layer and produce additional white light. The first optical assembly receives and substantially collimates the white light. The optical coupling element receives the substantially collimated white light from the first optical assembly and directs the light to an optical fiber. The optical fiber is then used to conduct the white light into an eye.

20 Claims, 9 Drawing Sheets

WHITE LIGHT EMITTING DIODE (LED) ILLUMINATOR FOR OPHTHALMIC ENDOILLUMINATION

This application claims priority to U.S. Provisional Application Ser. No. 61/233,285 filed on Aug. 12, 2009.

TECHNICAL FIELD OF THE INVENTION

The present disclosure relates to an illuminator for use in ophthalmic surgery and more particularly to an ophthalmic endoilluminator to produce a light suitable for illuminating the inside of an eye.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at the optical fiber that carries the light into the eye. The quality of this light is dependent on several factors including the types of optical elements selected.

SUMMARY OF THE INVENTION

The present disclosure provides an ophthalmic endoilluminator that substantially eliminates or reduces disadvantages and problems associated with previously developed systems. More specifically, the present disclosure provides an ophthalmic endoilluminator light source that fiber couples to an ophthalmic endoilluminator fiber to illuminate interior regions of the eye.

In one embodiment, the ophthalmic endoilluminator includes one or more white light emitting diodes (LEDs), an additional light source, a first optical assembly, an optical coupling element, and an optical fiber optically coupled to the optical coupling element. The white LED is capped with a phosphor layer. The additional light source illuminates at least a portion of an exterior surface of the phosphor layer within an absorption band of phosphor material of the phosphor layer in order to excite the phosphor layer and produce additional white light. The first optical assembly receives and substantially collimates the white light. The optical coupling element then receives the substantially collimated white light from the first optical assembly directs the light to an optical fiber. The optical fiber is then used to conduct the white light into an eye.

In another embodiment, the ophthalmic endoilluminator includes one or more white light emitting diodes (LEDs), an additional light source, a color adjustment light source, a first optical assembly, an optical coupling element, and an optical fiber optically coupled to the optical coupling element. The white LED is capped with a phosphor layer. The additional light source illuminates at least a portion of an exterior surface of the phosphor layer within an absorption band of phosphor material of the phosphor layer in order to excite the phosphor layer and produce additional white light. The first optical assembly receives and substantially collimates the white light. The color adjustment light source produces color adjustment light. The optical coupling element then receives the substantially collimated white light from the first optical assembly and the color adjustment light from the color adjustment light source and directs the combination of light to an optical fiber. The optical fiber is then used to conduct the white light into an eye.

In another embodiment, a method of generating white light with an LED for ophthalmic endoillumination is provided. This method involves first generating a white light by exciting a phosphor layer with at least one LED. The LED functions to illuminate an interior surface of the phosphor layer within an absorption band of phosphor material of the phosphor layer. Additional white light is generated by illuminating an exterior surface of the phosphor layer within an absorption band of phosphor material of the phosphor layer with an external light source. The two sources of white light are substantially collimated and optically coupled to an optical fiber to produce at least one optical output. The optical output couples to an ophthalmic endoilluminator fiber with an optical coupling element. This allows the optical output to illuminate an interior region of an eye.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DESCRIPTION OF THE INVENTION

Preferred embodiments of the present disclosure are illustrated in the FIGS., like numerals being used to refer to like and corresponding parts of the various drawings.

Embodiments of the present disclosure substantially address problems associated with illuminating the interior of the eye. More specifically, an ophthalmic endoilluminator is provided that includes one or more pump light emitting diodes (LEDs), an optical fiber, such as the scintillator fiber or fluorescent fiber. The optical fiber couples to the pump LEDs to receive an output of the LEDs and pass an optical output such as white light. The brightness of a white LED may be increased by irradiating a phosphor layer of the white LED from the front side with "additional pump" light from the front side. The additional pump light originates from any source, such as an LED or laser, and may be formatted (using condensing optics) to irradiate the entire phosphor layer, a portion of the phosphor layer, or an area larger than the phosphor layer. The optical fiber couples with an optical coupling element to the optical fiber receives the optical output and provides the optical output to an endoilluminator fiber which conducts the light into an interior region of the eye.

Figure 1:
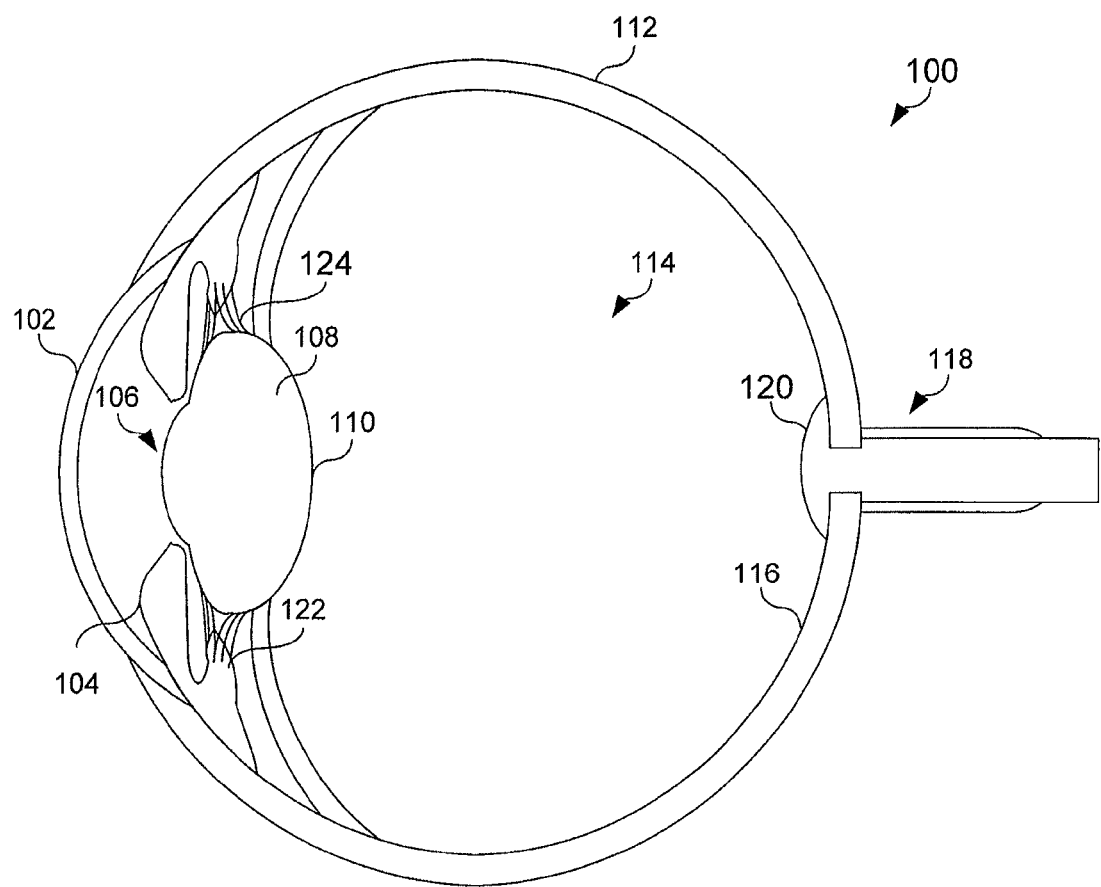
FIG. 1 illustrates the anatomy of the eye in which an Ophthalmic Endoilluminator in accordance with embodiments of the present disclosure may be placed.

Sight is, by far, one of our most valuable senses. Without our vision, everyday tasks like driving and reading books would be impossible. Our eyes are complex machines that deliver a clear picture of the world around us—communicating the simplest of colors, shapes and textures. FIG. 1 illustrates the anatomy of the eye into which the improved design for ocular implant provided by the present disclosure may be placed. Eye 100 includes cornea 102, iris 104, pupil 106, lens 108, lens capsule 110, zonules, ciliary body 120, sclera 112, vitreous gel 114, retina 116, macula, and optic nerve 120. Cornea 102 is a clear, dome-shaped structure on the surface of the eye acts as a window, letting light into the eye. Iris 104 is the colored part of the eye, called the iris, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The Ciliary body is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula is the area in the back of the eye that contains functions for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonular fibers 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

Ophthalmic endoilluminators have been previously based either on halogen tungsten lamps or high pressure arc lamps (metal-halides, Xe). The advantages of arc lamps are small emitting area (<1 mm), color temperature close to daylight, and longer life than in halogen lamps—400 hours vs. 50 hours. The disadvantage of arc lamps is high cost, decline in power, complexity of the systems and the need to exchange lamps several times over the life of the system.

An LED based illuminator provided by embodiments of the present disclosure may provide considerably lower cost and complexity, and characteristic life times of 50,000 to 100,000 hours that would allow operating ophthalmic fiber illuminator for entire life of the instrument with very little drop in output and without a need of exchanging LEDs.

Typical white LED consists of ultra violet (UV)/Violet/Blue LED exciting a white phosphor cap that emits white light. Currently all white LEDs could be considered spatially extended sources of illumination (3 mm diameter or so phosphor areas) with high numerical aperture. Thus current white LEDs are not suited well for coupling into a single fiber. Available pigtailed fiber illuminators based on white LEDs use fiber butted against LED phosphor. Only small fraction of light can be coupled into low numerical aperture and small diameter optical fiber. Therefore available pigtailed white LED sources deliver low levels of light. Embodiments of the present disclosure generate additional white light optical signals without the need to overdrive the LED by illuminating an exterior surface of a phosphor layer of a white LED with UV/Violet/Blue light.

Figure 2:
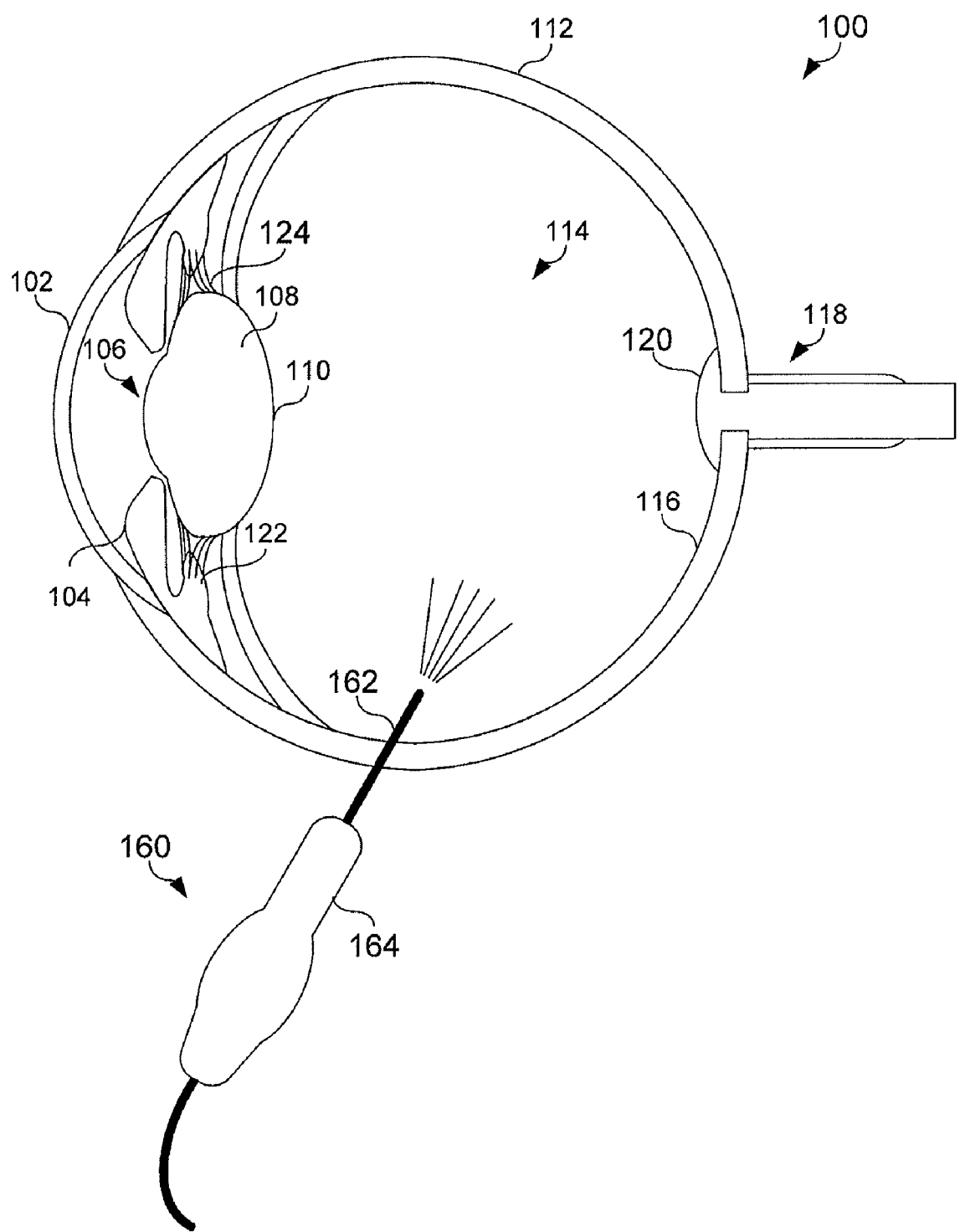
FIG. 2 illustrates and Ophthalmic Endoilluminator illuminating the interior of the eye in accordance with embodiments of the present disclosure.

FIG. 2 is cross section view of an ophthalmic endoilluminator 160 located in an eye according to an embodiment of the present disclosure. FIG. 2 depicts hand piece 164 and probe 162 in use. Probe 162 is inserted into eye 100 through an incision in the pars plana region. Probe 162 illuminates the inside or vitreous region 114 of eye 100. In this configuration, probe 162 can be used to illuminate the inside or vitreous region 114 during vitreo-retinal surgery.

The output of fiber coupled illuminators depends on the brightness of the light source and the coupling efficiency of the light into the fiber optic. As the physical size and/or numerical aperture of the fiber optic decreases, the brightness level of the source must increase proportionally in order to maintain the desired output through smaller fibers. This results in required source brightness levels that are higher than LEDs can provide. Hence, fiber-optic surgical illuminators in the past have relied upon high brightness sources (such as Xenon arc lamps, mercury vapor lamps, or metal halide lamps) to achieve enough light at the output of a fiber probe for surgery. White LEDs have several advantages for fiber-coupled surgical illumination applications, however, the present state of the art off the shelf white LEDs do not have brightness levels high enough to compete with these lamp sources without the use of brightness enhancements. Embodiments of the present disclosure describe an optical method of brightness enhancement that can push LED brightness beyond the threshold required for present day high power white LEDs to compete with lamp sources for ophthalmic illumination applications.

The simplest and most straightforward brightness enhancement for a white LED is to overdrive the LED by increasing the drive current to the LED junction beyond its rated drive current in order to achieve higher brightness. The lifetime of an LED is dependent (primarily) on two main operating parameters: operating temperatures, and current density, where increasing either or both parameters results in decreased LED lifetime. Hence, overdriving LEDs to achieve higher brightness levels, even with adequate cooling, is met with a tradeoff in LED lifetime.

Phosphor converted white LEDs create white light by coating a blue LED die with a phosphor layer. A portion of the blue light pumps the phosphor which provides broadband fluorescence that is predominantly yellow in color. The phosphor layer thickness is tuned such that a portion of blue light transmits through the phosphor layer to create white light. LED phosphors operate in an under saturated condition and hence, if more blue light is provided to the phosphor, be it from the underlying LED or another source, the brightness of the LED will be increased. Using a second pump source focused on the LED from the front side increases the brightness of the LED enabling the original LED to be run at lower drive currents. Using a second pump source enables the white LED to operate at lower drive currents, which thereby resulting in extended LED lifetime, while achieving the same brightness level as a single overdriven white LED.

In one example, as will be discussed with reference to FIG. 3, the output of a white LED is optically boosted, substantially collimated and directed into an optical fiber by condensing optics. The output of the white LED is produced from (1) an LED die illuminating an interior surface of a phosphor layer of the white LED within the absorption band of phosphor material of the phosphor; and (2) an external light source illuminating an exterior surface of a phosphor layer of the white LED within the absorption band of phosphor material of the phosphor. This result is increased optical output from the phosphor without the need to overdrive the LED die. The output is then easily coupled into a standard ophthalmic endoilluminator through ball lens or other optics. Note that the core diameter and numerical aperture may be chosen to be equal or smaller than that of endoilluminator.

Figure 3:
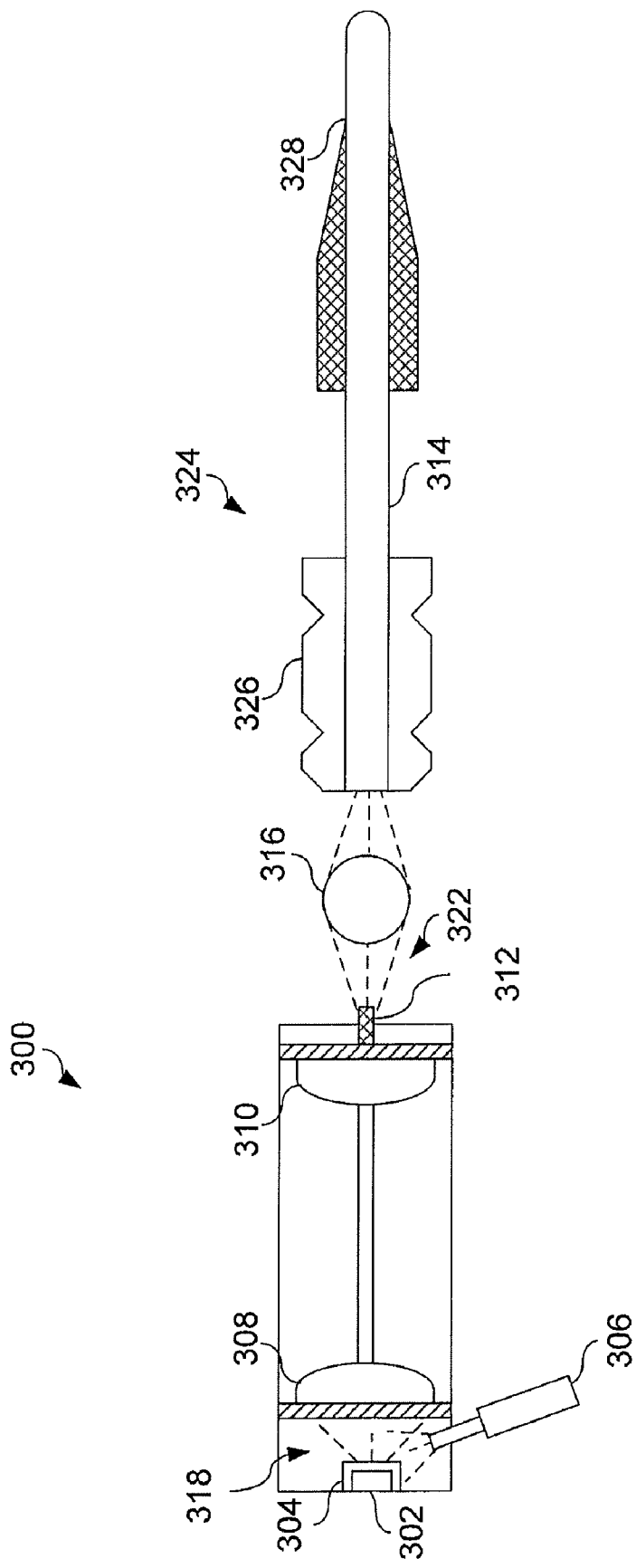
FIG. 3 is a cross-sectional diagram of a LED Ophthalmic Endoilluminator 300 in accordance with embodiments of the present disclosure.

FIG. 3 is a cross-sectional diagram of a LED Ophthalmic Endoilluminator 300 in accordance with embodiments of the present disclosure. Ophthalmic Endoilluminator 300 includes a LED 302, phosphor cap 304, secondary pump source 306 (i.e. blue or UV LED or laser, other LED, lamp source, etc), collimating optics 308, condensing optics 310 and optical fiber 312. Secondary pump source 306 irradiates the phosphor layer 304 of a white LED 302 with light within the absorption band of the phosphor material. Auxiliary pumping of the phosphor layer increases the brightness of the white LED source.

Additionally, optical fiber 312 may be a scintillator fiber is an optical fiber, in which the cladding and/or the core is luminescent. Such a fiber may be used to convert UV/Violet/Blue light illumination (pump) into broadband or white light through luminescence. Part of re-emitted white light propagates through scintillator fiber and can be either coupled to regular optical fiber or delivered to an illumination device directly.

Optical fiber 312 optically couples to an Ophthalmic Endoilluminator Fiber 314 through a ball lens 316 or other comparable optical system. The core diameter and numerical aperture of Optical fiber 312 may be chosen such that it is equal to or less than that of the optical fiber 314 within Ophthalmic Endoilluminator 324. The white light output 322 is directed through connector 316 and optical fiber 314 to probe 328 where it illuminates the inside of the eye 100. Embodiments of the present disclosure may utilize one or more LEDs to produce a constant and stable output 318. As is known, there are many types of LEDs with different power ratings and light output that can be selected as source 302.

An optional mirror may be a dichroic reflector that reflects visible wavelength light and only transmits infrared and ultraviolet light to produce a beam filtered of harmful infrared and ultraviolet rays. An optional mirror may reflect long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphakic hazard, blue light photochemical retinal damage and infrared heating damage, and similar light toxicity hazards. Typically, a light in the range of about 430 to 700 nanometers is preferable for reducing the risks of these hazards. Optional mirrors 308 and 316 are selected to allow light of a suitable wavelength to be emitted into an eye. Other filters and/or dichroic beam splitters may also be employed to produce a light in this suitable wavelength range.

The endoilluminator 324 that is handled by the ophthalmic surgeon includes an optical coupling 316, optical fiber 314, hand piece 326, and probe 328. Optical coupling 316 is designed to connect the optical fiber 314 to a main console (not shown) containing the light source 300. Optical coupling 316 properly aligns optical fiber 314 with the beam of light that is to be transmitted into the eye. Optical fiber 314 is typically a small diameter fiber that may or may not be tapered. Hand piece 326 is held by the surgeon and allows for the manipulation of probe 328 in the eye. Probe 328 is inserted into the eye and carries optical fiber 314 which terminates at the end of Probe 328. Probe 328 thus provides illumination from optical fiber 314 in the eye.

Embodiments of the present disclosure may also employ one or more fluorescent fibers which have been doped with red, green, and blue (RGB) organic dyes. This organic dye and UV LED pumping method is already known to those having skill in the art. For example three coils of such RGB fibers placed into an integrating sphere and illuminated with UV LEDs will create a strong RGB output. Then the individual RGB outputs may be combined onto a single fiber. This can be done in a multitude of ways such as but not limited to an RGB X prism, a dispersion prism, or a diffraction grading.

Figure 4:
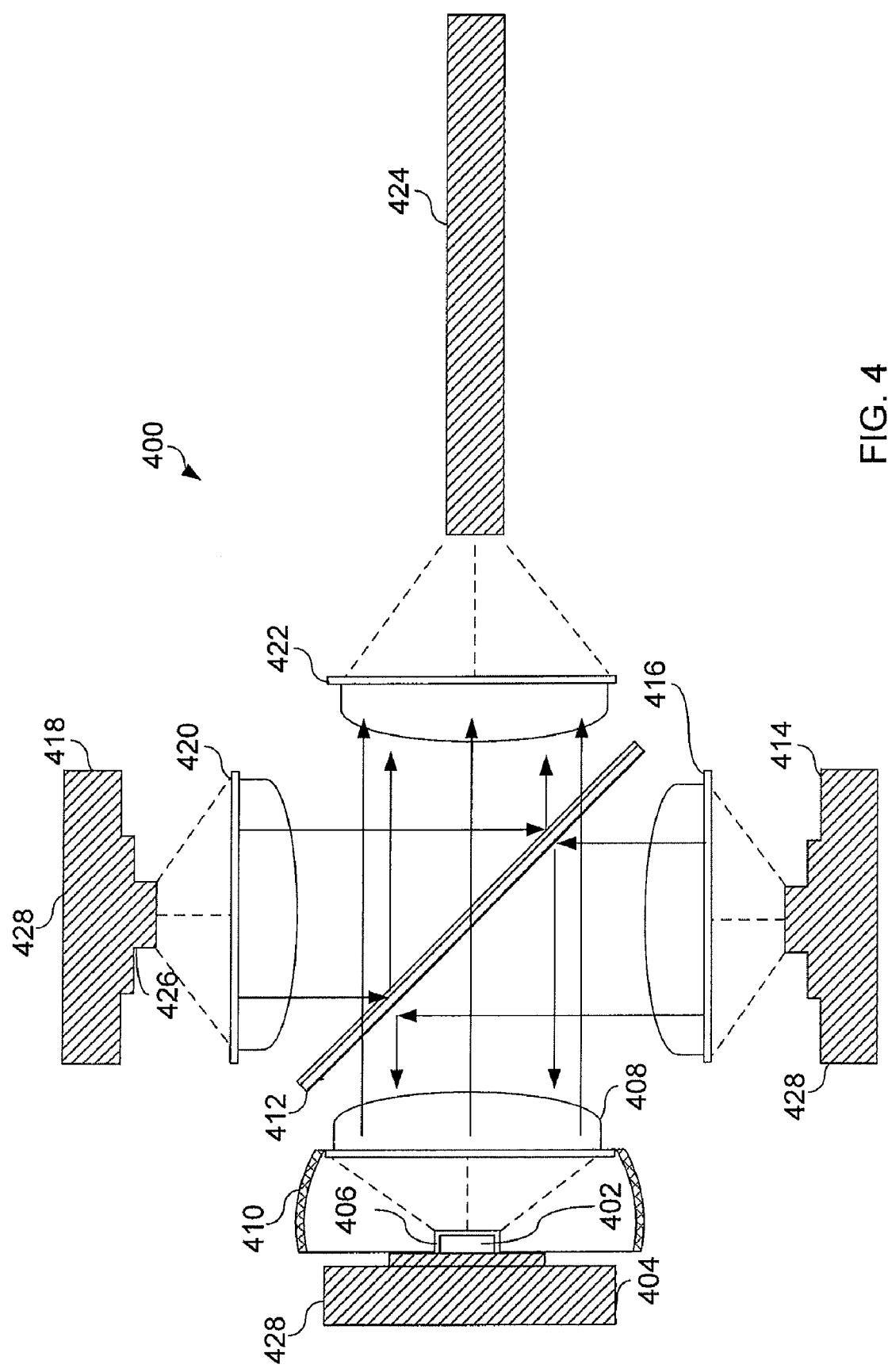
FIG. 4 is a functional diagram of a LED white light source for use with an Ophthalmic Endoilluminator in accordance with embodiments of the present disclosure.

Specific examples of optical boosting a white LED are given in FIGS. 4-7. FIGS. 4-7 utilize LED sources as secondary or auxiliary pump sources. These examples are based on Blue-Yellow illuminators, where light emitted from a blue LED is combined with the light emitted from the white LED for color adjustment. As an aside, color adjustment is required in most cases when a retro reflector is used for light recycling. The example shown in FIG. 4 is a compact design utilizing a single dichroic mirror for directing the secondary "boost" LED light toward the white LED while also providing a means of combining a blue LED with the output of the white LED.

FIG. 4 is a functional diagram of a LED white light source for use with an Ophthalmic Endoilluminator in accordance with embodiments of the present disclosure. FIG. 4 provides an example of optical boosting a white LED using a secondary blue or UV LED to pump the white LED while also using the same dichroic mirror for combining additional blue light into the white light path. White Light Source 400 includes white light LED 402, heat sink 404, the phosphor layer 406, collimating optics 408, optional retro reflector 410, dichroic mirror 412, a secondary light source 414, secondary collimating optics 416, color adjustment light source 418, tertiary collimating optics 420, condensing optics 422, and fiber probe 424.

LED 402 excites phosphor layer 406 to produce white light. However as previously stated this white light by itself may not be sufficient for uses in ophthalmic endoillumination. Therefore the phosphor layer 406 is further excited with an additional light source or secondary light source 414. This light source may generate UV or blue light that is redirected or reflected by dichroic mirror 412. This allows the collimating optics 408 to focus the light from the secondary light source onto the exterior surface of phosphor layer 406. This results in the production of additional white light which is substantially collimated by collimation optics 408 and passed by dichroic mirror 412. Condensing optics 422 then focuses the light to optical fiber 424 which may be optically coupled to an ophthalmic endoilluminator or optical probe. Additionally, color adjustment light in the form of blue light may be produced with light source 426 that is directed onto dichroic mirror 412 by collimating optics 420 where this blue light is reflected and not passed thus it combines with the passed white light and is focused into optical fiber 424 by collimating optics 422.

White Light Source 400 is a compact design using a single Dichroic Mirror 412 where Dichroic Mirror 412 reflects blue and UV light while transmitting white/yellow light. Thus the output of the Secondary Light Source 414 is reflected onto a Phosphor Layer 408 in order to produce additional white light. This additional white light is gathered and substantially collimating with Collimating Optics 408. When substantially collimated white light reaches Dichroic Mirror 412 the white light passes and may be focused by condensing Optic 422 to Fiber Probe 424.

Figure 5:
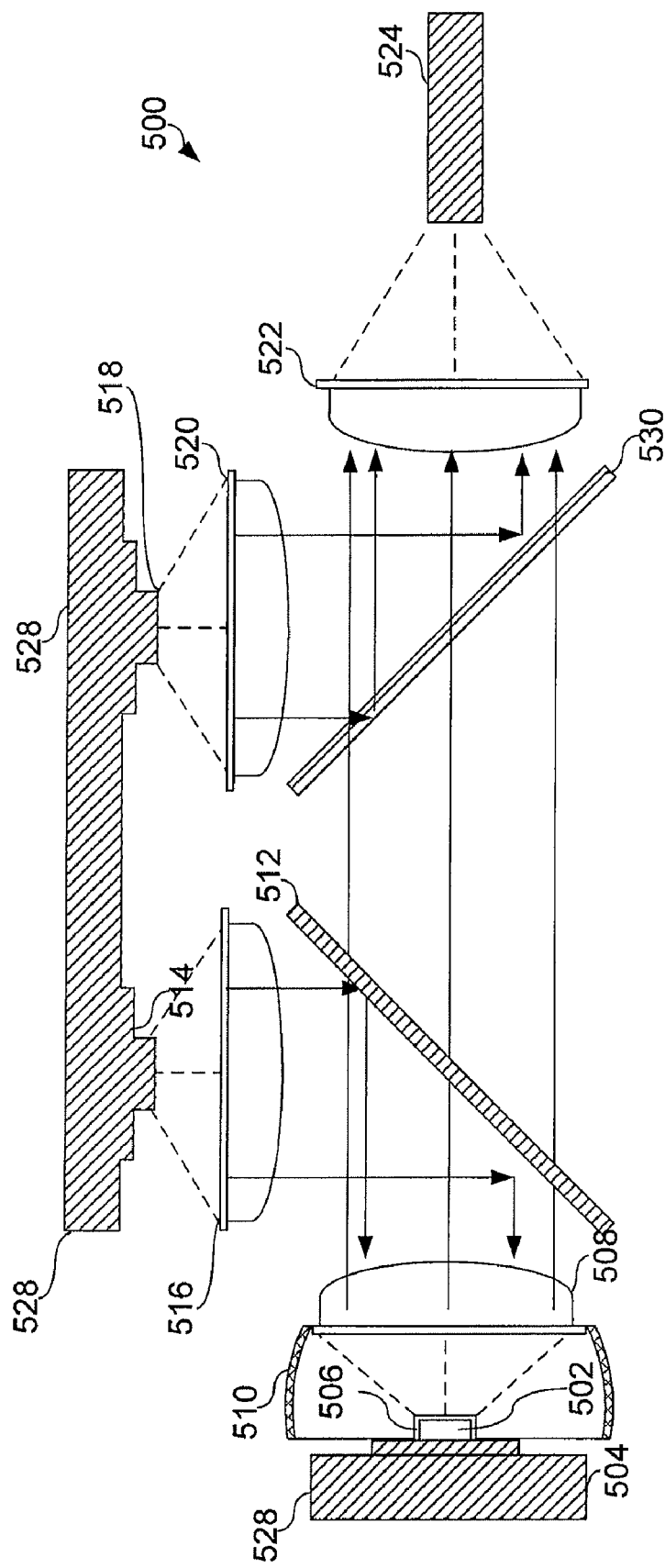
FIG. 5 is a functional diagram of a LED white light source for use with an Ophthalmic Endoilluminator in accordance with embodiments of the present disclosure.

FIG. 5 is a functional diagram of a LED white light source for use with an Ophthalmic Endoilluminator in accordance with embodiments of the present disclosure. FIG. 5 provides an example of optical boosting a white LED using a secondary blue or UV LED to pump the white LED where a single heatsink is used to cool both the boost LED and an additional blue LED for color adjustment.

White Light Source 500 includes white light LED 502, heat sink 504, the phosphor layer 506, collimating optics 508, optional retro reflector 510, dichroic mirror 512, a secondary light source 514, secondary collimating optics 516, color adjustment light source 518, tertiary collimating optics 520, condensing optics 522, fiber probe 524 and dichroic mirror 530.

The example shown in FIG. 5 is an alternative compact design utilizing a single heatsink element 528 for cooling both the "boost" LED 514 and an additional blue LED 518 that provides light for adjustment of white light. This design is advantageous when heat sinking can only be accomplished on one or two sides, when an additional heatsink element is cost prohibitive, or when the designed is space constrained in the direction normal to the optical axis. Note: for two port designs, a mirror image of the layout in FIG. 5 can be placed on the top side so that the heatsink between four LEDs can be shared.

Figure 6:
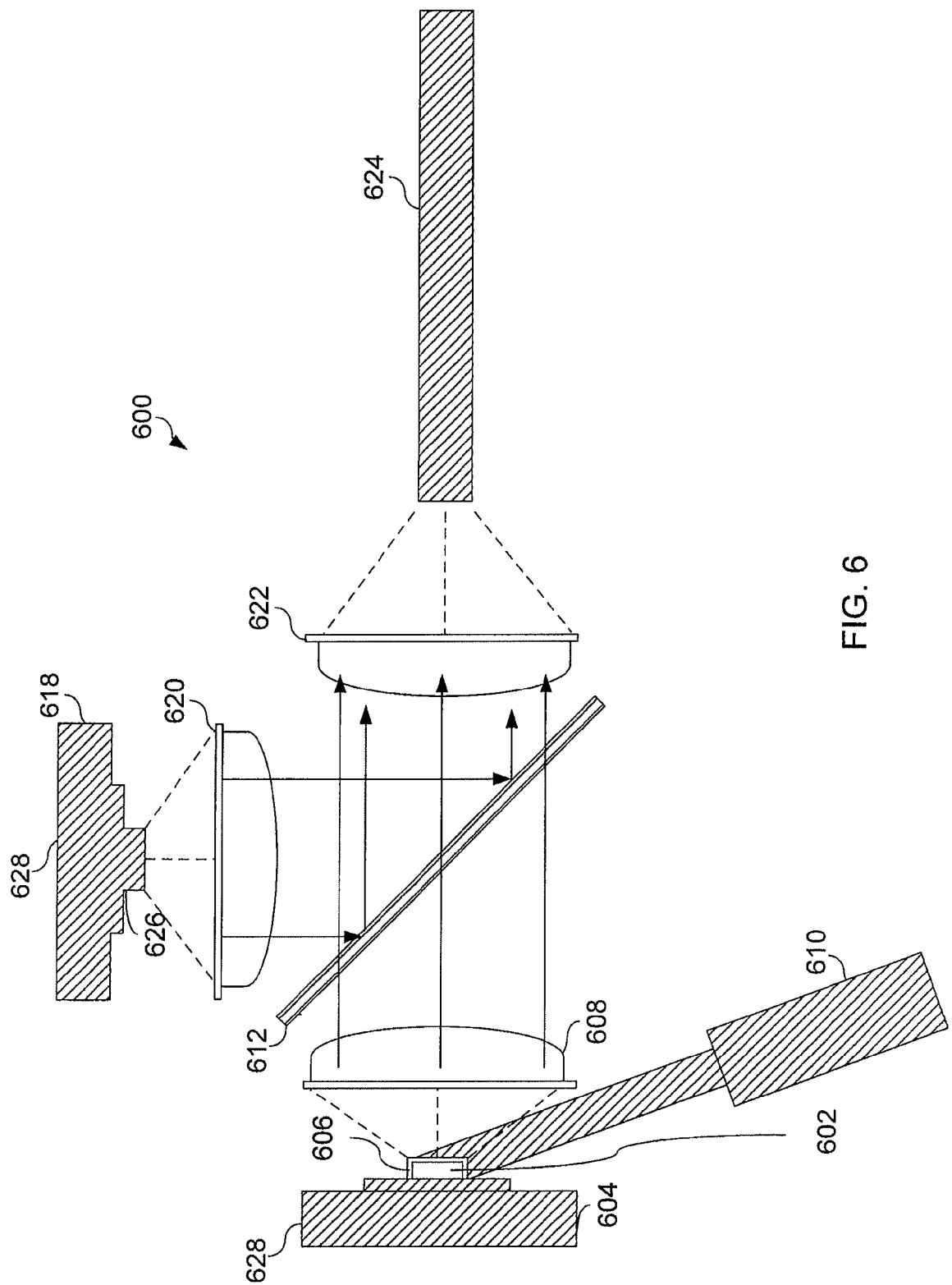
FIG. 6 is a functional diagram of a LED white light source for use with an Ophthalmic Endoilluminator in accordance with embodiments of the present disclosure.

FIG. 6 is a functional diagram of a LED white light source for use with an Ophthalmic Endoilluminator in accordance with embodiments of the present disclosure. FIG. 6 provides an example of optical boosting a white LED using a blue or UV laser diode to pump the white LED. An optional additional brightness enhancement using a full retro reflective mirror can also be used as shown. White Light Source 600 includes white light LED 602, heat sink 604, the phosphor layer 606, collimating optics 608, blue or UV laser diode 610, dichroic mirror 612, color adjustment light source 618, secondary collimating optics 620, condensing optics 622, fiber probe 624 and heat sink 628. The examples shown in FIGS. 6-7 utilize laser sources as secondary or auxiliary pump sources. The example shown in FIG. 6 utilizes a blue or UV laser diode 610 that is focused directly onto the white LED 602. In the case that additional pumping beyond what the blue or UV laser diode provides is required, a full retro reflective mirror for light recycling with a small hole for the beam to pass through can be used.

Figure 7:
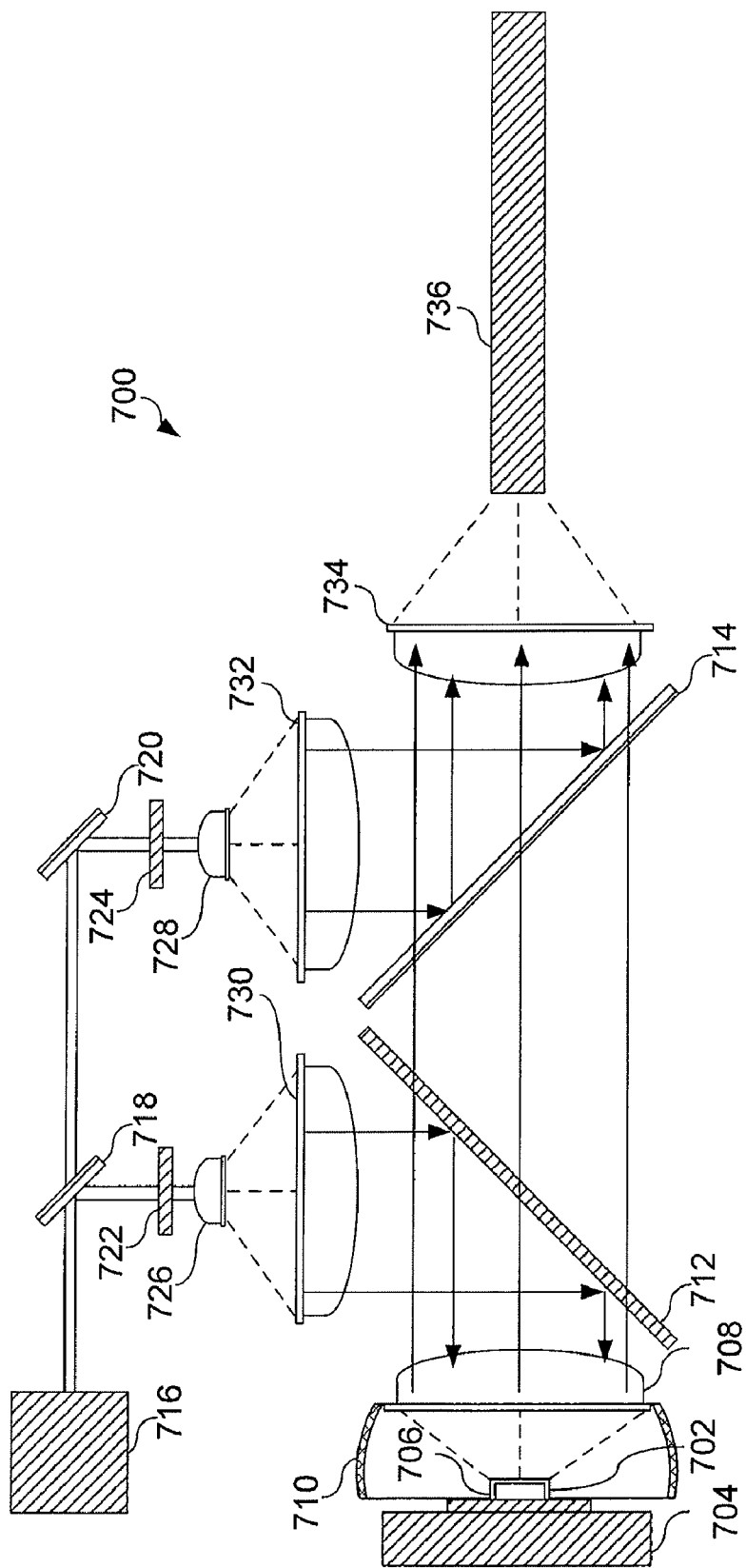
FIG. 7 is a functional diagram of a LED white light source for use with an Ophthalmic Endoilluminator in accordance with embodiments of the present disclosure.

FIG. 7 is a functional diagram of a LED white light source for use with an Ophthalmic Endoilluminator in accordance with embodiments of the present disclosure. FIG. 7 provides an example of optical boosting a white LED using a blue laser diode to pump the white LED and an option to provide additional blue light for color adjustment of the white beam. In this example attenuators are required for independent control of the blue LED. White Light Source 700 includes white light LED 702, heat sink 704, the phosphor layer 706, collimating optics 708, optional retro reflector 710, dichroic mirror 712, dichroic mirror 714, a laser light source 716, reflecting mirrors 718 and 720, attenuators 722 and 724, expanding lenses 726 and 728, secondary collimating optics 730, tertiary collimating optics 732, condensing optics 734, and fiber probe 736.

The example shown in FIG. 7 utilizes a blue laser diode 716 to provide both the "boost" light to the white LED 702 and additional blue light for color adjustment of the white beam. This example requires individual attenuators 722 and 724 in order to independently control the amount of light boosting the LED and combining with the white beam. The use of additional light for color adjustment is optional in this case, and method of pumping alone can be accomplished by making the beam splitting mirror 100% reflective and removing the downstream combining optics and both attenuators. However, this method may be expanded for dual port systems where light from a single blue laser diode can be split into four directions to "boost" two white LEDs and to provide light that is combined with the white LED light downstream. This is advantageous because the blue laser diode and both white LEDs can utilize the same heatsink.

Figure 8:
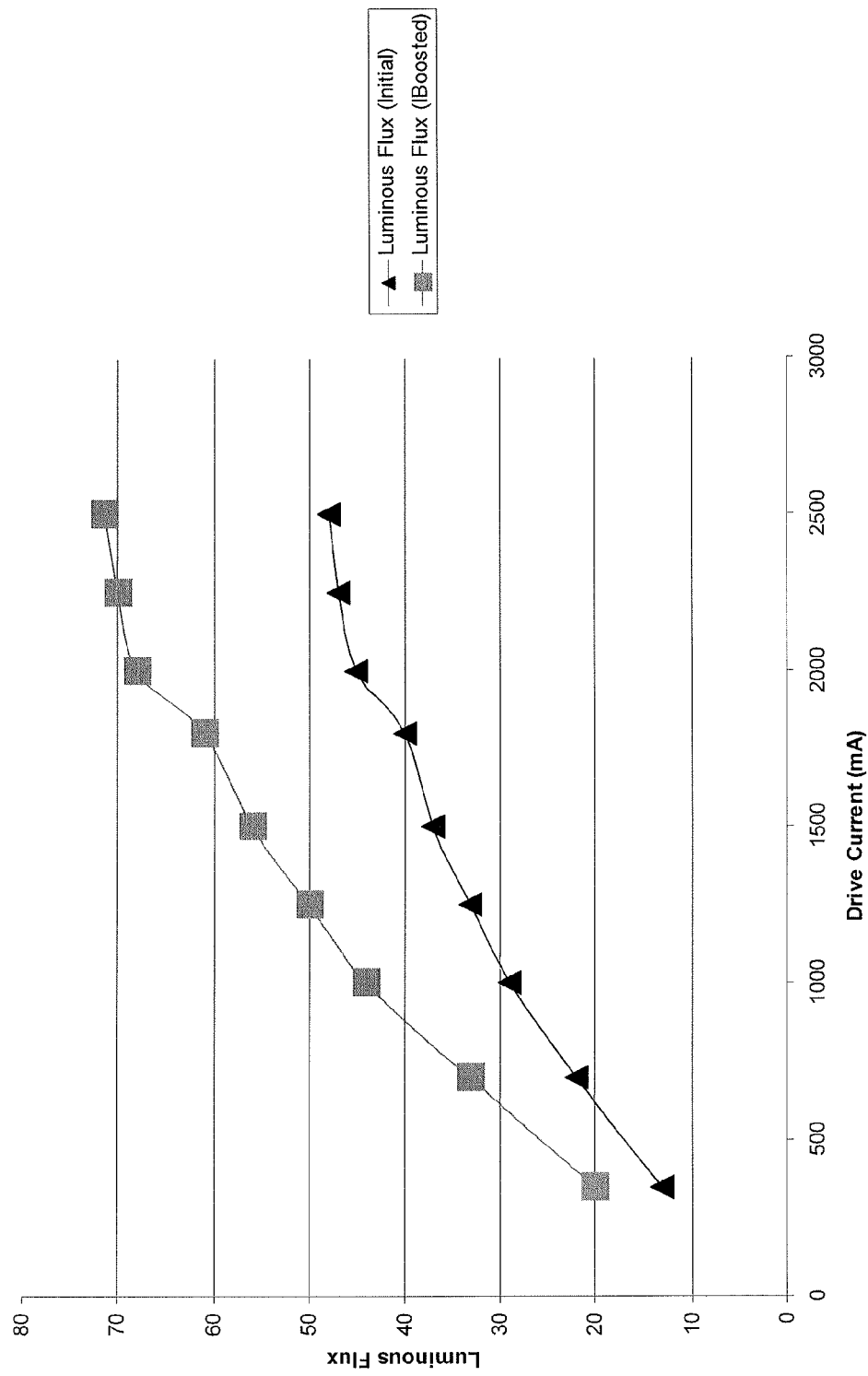
FIG. 8 provides a chart comparing the expected performance a LED illuminator utilizing an undomed blue LED driven at the same drive current as the white LED.

FIG. 8 provides a chart comparing the expected performance a LED illuminator utilizing an undomed blue LED driven at the same drive current as the white LED. As one can see, there is an additional 54% boost using the method described within this disclosure where a single blue LED driven at the same drive current as the white LED is used to "boost" the white LED.

Figure 9:
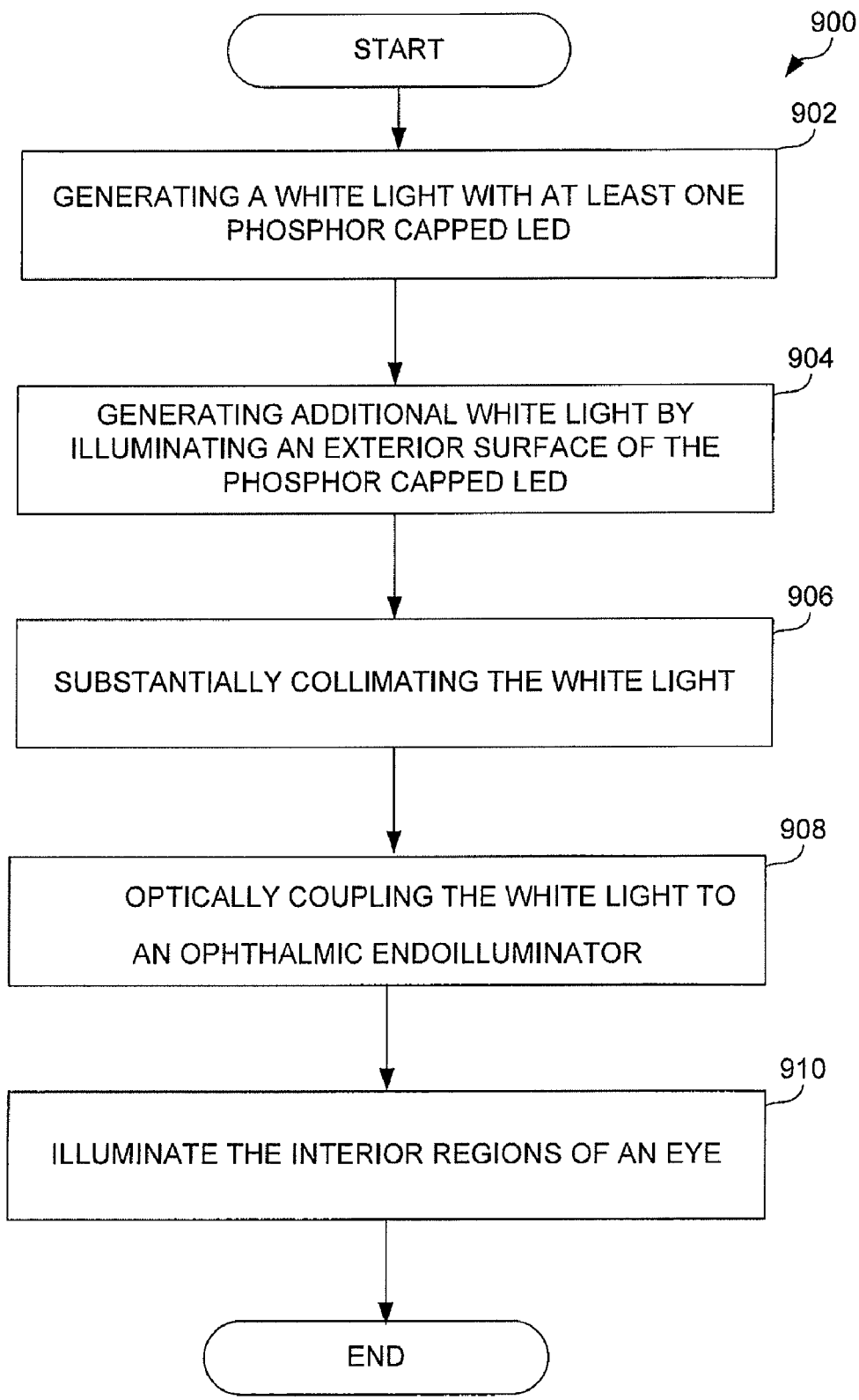
FIG. 9 provides a logic flow diagram associated with a method of illuminating the interior vitreous regions of an eye using an ophthalmic endoilluminator in accordance with embodiments of the present disclosure.

FIG. 9 provides a logic flow diagram associated with a method of illuminating the interior vitreous regions of an eye using an ophthalmic endoilluminator in accordance with embodiments of the present disclosure. Operation 900 began with block 902 where white light is generated with at least one white LED. For the reasons stated above, the white LED may not on its own generate sufficient light for the ophthalmic endoilluminator. Thus, in Block 904 additional white light may be generated by illuminating an exterior surface of the white LED in order to excite the phosphor layer and produce additional white light. The white light including both the white light generated from the LED and the white light generated by illuminating the external surface of the white LED is substantially collimated in Block 906. Block 908 optically couples this white light to an ophthalmic endoilluminator which in Block 910 may be used to eliminate the interior regions of an eye. This allows the optical fiber of the ophthalmic endoilluminator to conduct white light or other wave lengths generated to illuminate the interior regions of an eye in block 910.

As previously stated the pump source may provide an output to one or more scintillating or fluorescent optical fibers. When a fluorescent optical fiber is used this fiber may be doped with red, green or blue organic dyes. This allows the fluorescent fiber to produce an RGB optical output. The pump source and the scintillating fluorescent or optical fibers may be placed within a light pipe having mirrors on both ends of the having reflectors to allow for multiple reflections and pumping of the radiation produced by the pumping source. In other embodiments the scintillating fiber may be placed in a UV reflective integrating sphere or a light type for further pumping. The reflective surfaces mirrors at the distal end of the scintillating or fluorescent fibers reflect light within the scintillating or fluorescent optical fibers to produce light in a common output direction while passing the output of the pump source to the clad or core doped fiber.

In block 908, the output is directed to an ophthalmic endoilluminator fiber and may involve combining the optical output from multiple sources. In such an instance an optical combining element such as a ball lens, X-prism, dispersion prism or diffraction grating may be used to combine these optical signals into a single optical signal placed on the optical fiber of the ophthalmic endoilluminator. The core diameter and numerical aperture of the fiber on which the combined outputs of the one or more scintillating or fluorescent fibers is provided is equal to or smaller than that of the ophthalmic endoilluminator fiber.

In summary, embodiments provide an ophthalmic endoilluminator. From the above, it may be appreciated that the present disclosure provides an improved system for illuminating the inside of the eye. The ophthalmic endoilluminator includes one or more white LEDs, an additional light source, a first optical assembly, an optical coupling element, and an optical fiber optically coupled to the optical coupling element. The white LED is capped with a phosphor layer. The additional light source illuminates at least a portion of an exterior surface of the phosphor layer within an absorption band of phosphor material of the phosphor layer in order to excite the phosphor layer and produce additional white light. The first optical assembly receives and substantially collimates the white light. The optical coupling element then receives the substantially collimated white light from the first optical assembly directs the light to an optical fiber. The optical fiber is then used to conduct the white light into an eye.

The present disclosure is illustrated herein by example, and various modifications may be made by a person of ordinary skill in the art. Although the present disclosure is described in detail, it should be understood that various changes, substitutions and alterations can be made hereto without departing from the spirit and scope of the disclosure as described.

What is claimed is:

1. An ophthalmic endoilluminator comprising:
   at least one white Light Emitting Diode (LED), the at least one white LED comprising a phosphor layer;
   at least one additional light source operable to illuminate at least a portion of an exterior surface of the phosphor layer within an absorption band of phosphor material of the phosphor layer;
   a first optical assembly operable to receive and substantially collimate the white light from the at least one LED;
   an optical coupling element, the optical coupling element operable to receive the substantially collimated white light from the first optical assembly; and
   an optical fiber optically coupled to the optical coupling element, the optical fiber operable to conduct the white light into an eye.

2. The ophthalmic endoilluminator of claim 1, wherein the at least one white LED comprises an LED die coated with the phosphor layer, the LED die operable to illuminate at least a portion of an interior surface of the phosphor layer within the absorption band of phosphor material of the phosphor.

3. The ophthalmic endoilluminator of claim 2, the LED die comprising a UV or Blue light LED die.

4. The ophthalmic endoilluminator of claim 1, further comprising:
   a color adjustment light source, operable to produce color adjustment light;
   an optical element operable to:
      receive the color adjustment light from the color adjustment light source; and
      combine the color adjustment light with the white light; and
   the optical coupling element operable to:
      receive and pass the combined color adjustment light and white light to the optical fiber.

5. The ophthalmic endoilluminator of claim 4, the color adjustment light source comprising a blue LED.

6. The ophthalmic endoilluminator of claim 1, further comprising a first dichroic mirror, the first dichroic mirror operable to reflect an output of the additional light source towards the surface of the phosphor layer and pass the substantially collimated white towards the optical coupling element.

7. The ophthalmic endoilluminator of claim 6, further comprising a color adjustment light source, the first dichroic mirror operable to reflect an output of the color adjustment light source towards the optical coupling element.

8. The ophthalmic endoilluminator of claim 6, further comprising:
   a color adjustment light source; and
   a second dichroic mirror, the second dichroic mirror operable to:
      reflect an output of the color adjustment light source towards the optical coupling element; and
      pass the substantially collimated white towards the optical coupling element.

9. An ophthalmic endoilluminator comprising:
   at least one white Light Emitting Diode (LED), the at least one white LED comprising a phosphor layer;
   at least one additional light source operable to illuminate at least a portion of an exterior surface of the phosphor layer with UV or Blue light within an absorption band of phosphor material of the phosphor layer;
   a color adjustment light source, operable to produce color adjustment light;
   a first optical assembly operable to receive and substantially collimate the white light from the at least one LED;
   at least one optical element, the at least one optical element operable to combine the substantially collimated white light from the first optical assembly and the color adjustment light from the color adjustment light source;
   an optical coupling element operable to receive the combined color adjustment light and white light; and
   an optical fiber optically coupled to the optical coupling element, the optical fiber operable to:
   conduct the combined color adjustment light and white light to an optical probe of the ophthalmic endoilluminator.

10. The ophthalmic endoilluminator of claim 9, wherein the at least one white LED comprises an LED die coated with the phosphor layer, the LED die operable to illuminate at least a portion of an interior surface of the phosphor layer within the absorption band of phosphor material of the phosphor.

11. The ophthalmic endoilluminator of claim 10, the LED die comprising a UV or Blue light LED die.

12. The ophthalmic endoilluminator of claim 9, the at least one optical element comprising:
   a dichroic mirror operable to pass the white light and reflect the color adjustment light to combine the color adjustment light and the white light.

13. The ophthalmic endoilluminator of claim 12, the dichroic mirror operable to reflect the UV or Blue light from the at least one additional light source to illuminate the at least the portion of the exterior surface of the phosphor layer.

14. The ophthalmic endoilluminator of claim 12, the at least one optical element further comprising a second dichroic mirror operable to pass white light and reflect the UV or Blue light from the at least one additional light source to illuminate the at least the portion of the exterior surface of the phosphor layer.

15. A method comprising:
   generating a white light by exciting a phosphor layer with at least one LED operable to illuminate an interior surface of the phosphor layer within an absorption band of phosphor material of the phosphor layer;
   generating additional white light by illuminating an exterior surface of the phosphor layer within an absorption band of phosphor material of the phosphor layer with an external light source;
   substantially collimating the white light;
   optically coupling the white light to at least one optical fiber to produce at least one optical output;
   optically coupling the at least one optical output to an ophthalmic endoilluminator fiber with an optical coupling element; and
   conducting the optical output with the ophthalmic endoilluminator fiber to illuminate an interior region of an eye.

16. The method of claim 15, the at least one LED comprises an LED die coated with the phosphor layer, the LED die operable to illuminate at least a portion of an interior surface of the phosphor layer within the absorption band of phosphor material of the phosphor.

17. The method of claim 16, the LED die comprising a UV or Blue light LED die.

18. The method of claim 15, further comprising:
   producing color adjustment light; and
   combining the color adjustment light with the white light.

19. The method of claim 18, the color adjustment light produced from a blue LED.

20. The method of claim 15, further comprising reflecting the output of the external light source towards the phosphor layer with a first dichroic mirror, the first dichroic mirror operable to reflect an output of the external light source towards the phosphor layer and pass the substantially collimated white light.

* * * * *